United States Patent [19]
Hsia et al.

[11] Patent Number: 5,598,426
[45] Date of Patent: Jan. 28, 1997

[54] METHOD AND DYE LASER APPARATUS FOR PRODUCING LONG PULSES OF LASER RADIATION

[75] Inventors: James C. Hsia, Andover; Rafael A. Sierra, Palmer, both of Mass.

[73] Assignee: Candela Laser Corporation, Wayland, Mass.

[21] Appl. No.: 383,412

[22] Filed: Feb. 3, 1995

[51] Int. Cl.$^6$ ................................ H01S 3/20
[52] U.S. Cl. ............................ 372/53; 372/38
[58] Field of Search ................ 372/38, 53, 70

[56] References Cited

U.S. PATENT DOCUMENTS

| | | |
|---|---|---|
| 3,178,657 | 4/1965 | Morse . |
| 3,760,295 | 9/1973 | Lankard et al. . |
| 3,829,791 | 8/1974 | Schwartz . |
| 3,863,105 | 1/1975 | Ewanizky . |
| 3,914,709 | 10/1975 | Pike et al. . |
| 4,398,129 | 8/1983 | Logan . |
| 4,445,217 | 4/1984 | Acharekar et al. ............... 372/53 |
| 4,525,842 | 6/1985 | Myers . |
| 4,566,107 | 1/1986 | Kitaura et al. ............... 372/38 |
| 4,627,063 | 12/1986 | Hosokawa . |
| 4,829,262 | 5/1989 | Furumoto . |
| 4,860,302 | 8/1989 | Janes . |
| 4,891,817 | 1/1990 | Duarte ............... 372/53 |
| 4,917,084 | 4/1990 | Sinofsky . |
| 4,981,138 | 1/1991 | Deckelbaum et al. . |
| 5,041,108 | 8/1991 | Fox et al. . |
| 5,066,293 | 11/1991 | Furumoto . |
| 5,195,104 | 3/1993 | Geiger et al. . |
| 5,287,380 | 2/1994 | Hsia . |
| 5,343,483 | 8/1994 | Farrell et al. ............... 372/38 |

OTHER PUBLICATIONS

Pappalardo et al.; "Long–Pulse Laser Emission from Rhodamine 6G", IEEE Journal of Quantum Elec., vol. QE–6, No. 11, (1970) No Month.

Levin et al.; "Photostability of Aqueous Micellar Solutions of Rhodamines Under Flash Lamp Excitation", Opt. Spectrosc. (USSR) 60(4) (1986) No Month.

Pavlopoulos et al.; "Laser Action from 2, 6, 8–position Trisubstituted 1, 3, 5, 7–tetramethylpyrromethene–BF$_2$", Applied Optics, vol. 29 (27) (1990) No Month.

*Primary Examiner*—Rodney B. Bovernick
*Assistant Examiner*—Robert E. Wise
*Attorney, Agent, or Firm*—Testa, Hurwitz & Thibeault, LLP

[57] ABSTRACT

A flashlamp-excited dye laser generates a pulsed output beam having a long pulse duration. The laser includes a pulse forming circuit which generates an excitation pulse having an amplitude which generally increases in coordination with the lasing threshold for the flashlamp-excited dye laser. The flashlamp-excited dye laser is driven with the pulse to produce a pulsed output beam of laser radiation of at least 500 microseconds in duration.

14 Claims, 3 Drawing Sheets

62 →

RHODAMINE 575

64 →

RHODMINE 590
(CHLORIDE)

METHOD AND DYE LASER APPARATUS FOR PRODUCING LONG PULSES OF LASER RADIATION

FIELD OF THE INVENTION

This invention relates in general to the field of lasers. More specifically, to an improved method and dye laser apparatus for producing a pulsed beam of laser radiation of long pulse duration.

BACKGROUND

Certain medical procedures utilizing flashlamp-excited dye lasers can achieve more optimal results by employing a laser which generates a pulsed output beam having a relatively long pulse duration. One such medical technique is selective photothermolysis, in which targeted tissue which includes a pigmentation abnormality (e.g., a vascular lesion, pigmented lesion or tattoo) is heated by pulses of laser radiation having a wavelength specifically selected to be absorbed by the targeted tissue. The benefits afforded by using a flashlamp-excited dye laser which generates a pulsed output beam having a relatively long pulse duration include improved clearance of the lesion, fewer treatment sessions and reduced incidence of purpura, hypopigmentation and hyperpigmentation.

Conventional flashlamp-excited dye lasers produce pulsed output beams having a pulse duration on the order of 0.1 to 100 microseconds. Attempts to extend the pulse duration typically results in an accumulation of dye molecules in metastable electronic states and thermal distortions in the liquid dye medium (i.e., the gain medium), which cause the laser action (i.e. lasing) to self-terminate. These phenomena are induced, in general, by the excitation energy provided to the dye medium by the flashlamp.

Dye molecules that become excited from a ground state to metastable electronic states during excitation of the dye medium do not return readily to the ground state. Instead, these dye molecules may absorb a photon whose wavelength lies in the operating region the laser pulse. Thus, these molecules no longer contribute to the gain medium and act to inhibit laser action. The addition of cyclotetraene (COT) or diazobicyclooctane (DABCO) to the liquid dye medium effectively quenches these molecules, enabling the laser to generate pulses in excess of a few tens of microseconds. To slow the adverse effects of thermal distortions in the liquid dye medium, a laser with an optical system having a reduced thermal sensitivity can generate pulses up to a few hundred microseconds in duration.

Another limitation to extended pulse durations is the photodegradation of the dye caused by the excitation pulses. There are two aspects to photodegradation: photobleaching which decreases available gain and produces harmful photoproducts. Photobleaching of the dye is when some portion of the dye molecules are destroyed during pulse generation and can no longer participate in the lasing process. The destroyed dye molecules are commonly converted to byproducts that absorb radiation at the laser wavelength and inhibit lasing. As a result of photobleaching, the available gain in the liquid dye medium decreases and the lasing threshold (i.e., the energy level at which oscillation or laser action occurs) rises. As such, the minimum input pulse amplitude (or energy level) needed to achieve the lasing threshold and sustain the pulse rises rapidly. For an input pulse with a constant amplitude, the lasing threshold rapidly exceeds the input pulse amplitude causing laser action to terminate in a few hundred microseconds. A laser utilizing a ramped excitation pulse (i.e., increasing in amplitude during the entire duration of the pulse) to drive the flashlamp can sustain longer pulses in many instances. However, a ramped excitation pulse may not be optimal for a laser utilizing certain dyes.

SUMMARY OF THE INVENTION

The present invention features a method and apparatus for generating a pulsed output beam having a long pulse duration (e.g. at least 500 microseconds) using a flashlamp-excited dye laser. The invention recognizes that driving the flashlamp with an excitation pulse from a pulse forming circuit having an amplitude increasing in coordination with increases in the lasing threshold of the lasing medium produces a pulsed output beam having a long duration in an energy efficient manner. The invention also recognizes that utilizing dyes having a molecular structure comprising at least one electron-pair donor may result in a pulsed output beam having a longer duration than other dyes.

In one embodiment, the invention features a method of generating a pulsed beam of laser radiation having a long pulse duration using a flashlamp-excited dye laser. An excitation pulse having an amplitude which generally increases in coordination with the lasing threshold for the flashlamp-excited dye laser is generated. More specifically, the pulse may initially have a generally constant amplitude in coordination with a generally constant laser threshold, followed by an increasing amplitude in coordination with an increasing lasing threshold. The flashlamp-excited dye laser is driven with the pulse to produce a pulsed output beam of laser radiation of at least 500 microseconds in duration.

The flashlamp-excited dye laser may include a dye having a molecular structure which comprises at least one electron-pair donor (i.e., a Lewis base). The at least one electron-pair donor may be a carboxyl group, specifically a carboxylate ion. The dye may disposed in a liquid and may further comprise at least one electron-pair acceptor. In one detailed embodiment, the dye is Rhodamine 575.

In another embodiment, the invention features a flashlamp-excited dye laser for producing a pulsed beam of laser radiation having a long duration. To accomplish this, the laser includes a pulse forming circuit which energizes the flashlamp by providing an excitation pulse having an amplitude which generally increases in coordination with the lasing threshold for the flashlamp-excited dye laser. In particular, the pulse initially has a generally constant amplitude followed by an increasing amplitude in coordination with an increasing lasing threshold. The laser produces a pulsed output beam of at least 500 microseconds in duration. Experiments have shown such a laser can generate a pulsed output beam of at least one millisecond in pulse duration.

Other aspects, features, and advantages of the invention will become apparent from the following description and from the claims.

DETAILED DESCRIPTION

Figure 1:
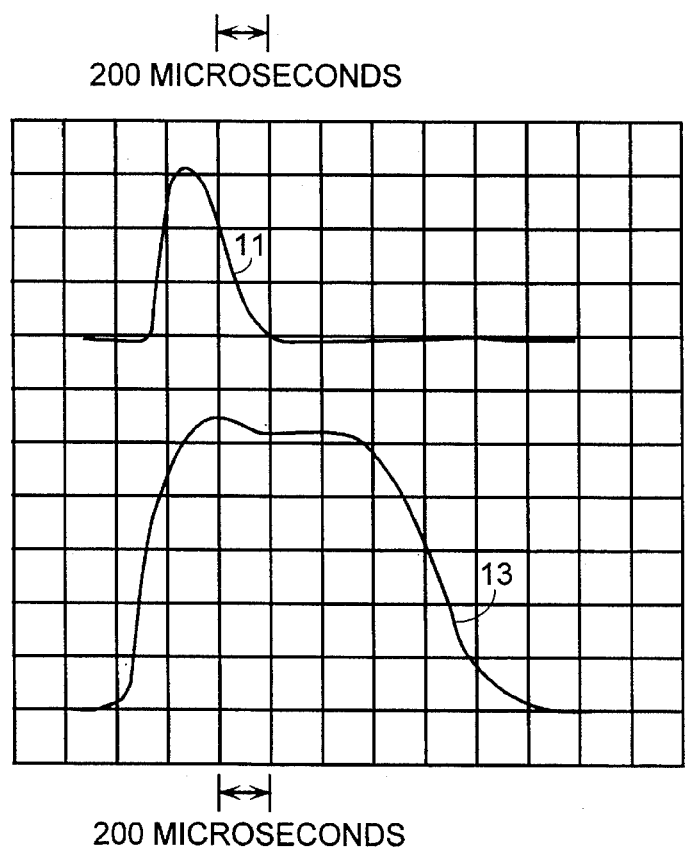
FIG. 1 is a graphical illustration of an excitation pulse applied to, and an output pulse produced by, a conventional laser system.

Referring to FIG. 1, in a conventional flashlamp-excited laser system, an input or excitation pulse 11 provided to a flashlamp typically is approximately constant and the duration of a resulting output laser pulse 13 typically is about 400 microseconds or less. As is typical in such conventional laser systems, the output pulse initially increases but then rapidly decreases while the excitation pulse is held relatively constant. Thus, as shown, such conventional laser systems have a tendency to self-terminate or quench because the lasing threshold cannot be maintained for longer than about 400 microseconds when a relatively constant input pulse such as the excitation pulse is applied.

Figure 2:
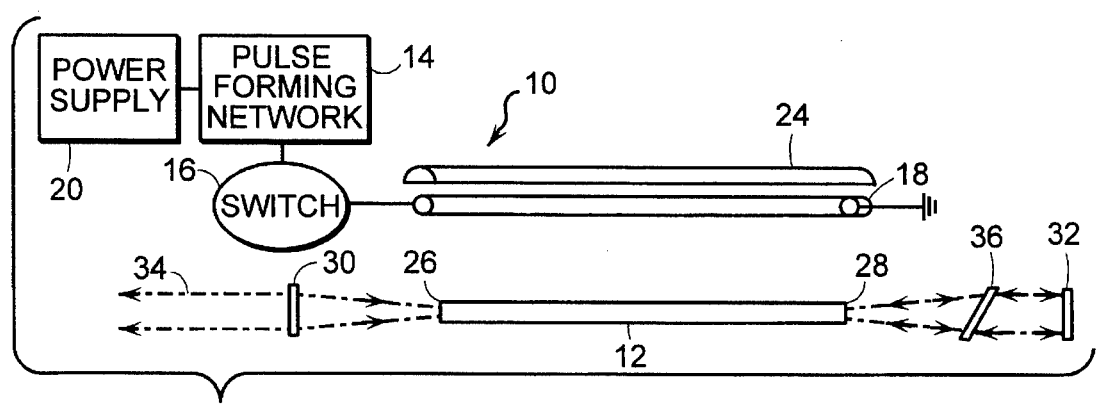
FIG. 2 is a functional block diagram of laser system generating a pulsed output beam having a long pulse duration in accordance with the invention.

Referring to FIG. 2, a laser system in accordance with the invention includes a flashlamp-excited laser 10. In this embodiment, a lasing medium in the form of a dye carried by a liquid is directed through an elongated dye cell 12 from one end to the other. The lasing medium typically is maintained at a uniform and constant temperature. A power supply 20 provides energy to a pulse forming network 14. The pulse forming network 14 generates an excitation pulse and applies the pulse, typically through a switching device 16, such as an ignitron or SCR, to a flashlamp 18 to excite the lasing medium. The current pulse generated by the network causes the flashlamp to discharge, producing light of high intensity. The particular circuitry details for the network according to the invention can be realized in a variety of ways readily ascertainable by one of ordinary skill in circuit design.

The light of high intensity emanating from the flashlamp is directed to the lasing medium in the dye cell by, for example, a focused reflector 24. The light from the flashlamp is absorbed by the lasing medium and molecules in the lasing medium move from the ground state to excited singlet states. As the excited molecules return to the ground state, photons of a particular wavelength are emitted. Some of the light emanates from apertures 26, 28 located at each end of the dye cell. First and second mirrors 30, 32, in combination constitute an optical system for the laser. The first mirror, which is fully reflective, returns emanated light back into the dye cell. A second mirror, which is partially transmissive, returns some of the emanated light but allows a portion to escape.

The light resonates between the mirrors and increases in intensity until it reaches the lasing threshold. At that point, a measurable amount of light passes through the second mirror as a laser pulsed output beam 34. As explained in detail below, the lasing threshold is generally constant for the initial portion of the output pulse and increases during the latter portion thereof. In accordance with the invention, the pulse forming network provides an excitation pulse having a generally constant amplitude initially and an increasing amplitude in coordination with the increasing laser threshold. The result is a pulsed beam of laser radiation having a duration of at least 500 microseconds. Experiments have produced pulses on the order of milliseconds.

Figure 3:
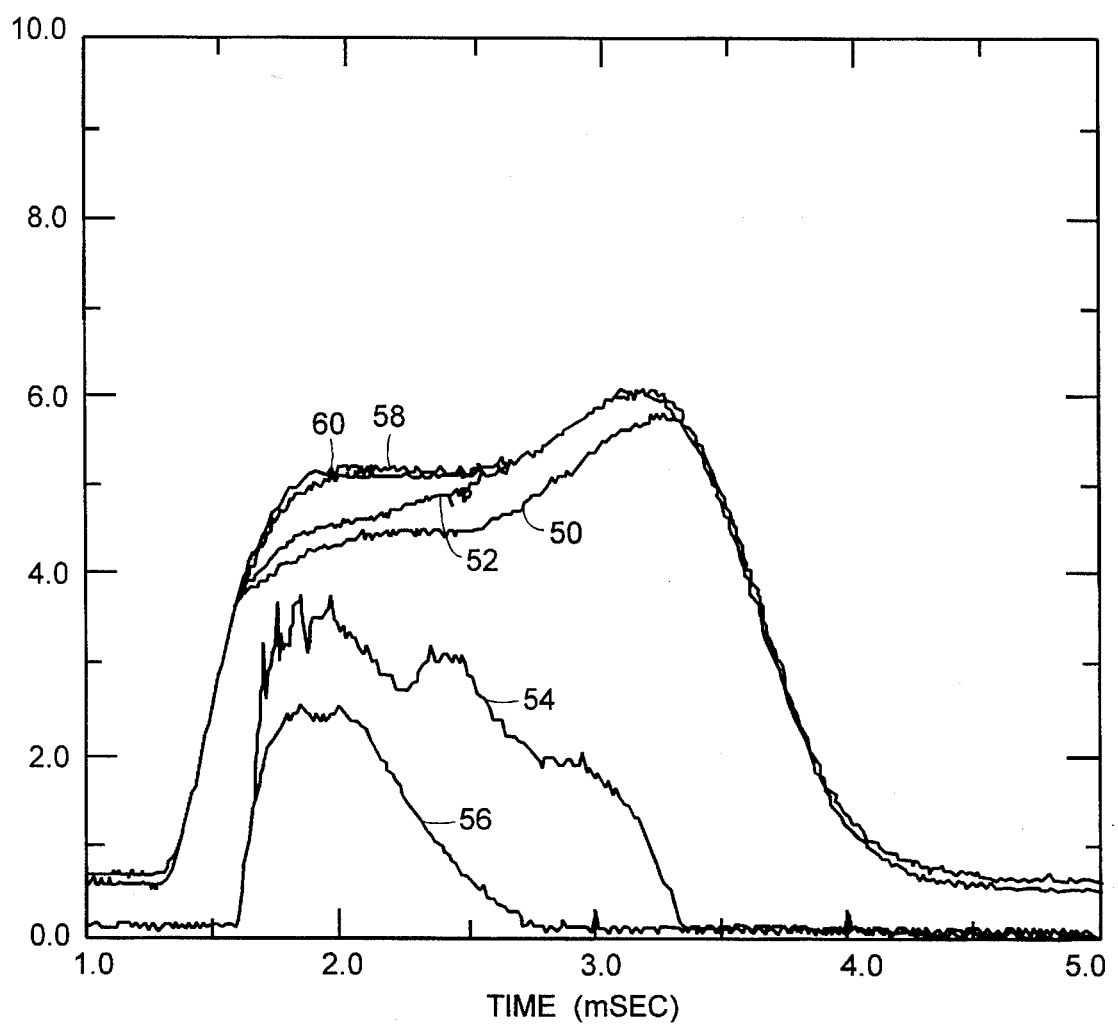
FIG. 3 is a graphical illustration of an excitation pulse according to the invention and an output pulse of extended duration produced by the laser system of FIG. 1.

FIG. 3 is a graphical illustration of the performance of two closely related laser dyes, Rhodamine 575 and Rhodamine 590, under nearly identical pulse excitation conditions. The curves 50 and 52 show the minimum excitation pulse amplitude required to achieve lasing (i.e., the laser threshold). Also shown are the resulting laser output pulse curves 54 and 56 corresponding to each of the two dyes. Also shown is the excitation pulse curves 58 and 60 used for a laser incorporating the two dyes.

As shown, the minimum excitation pulse 58 required to achieve lasing is at first the same for both dyes, then rising rapidly for Rhodamine 590, but initially only modestly for Rhodamine 575. Thus, for Rhodamine 575 during the first 800 microseconds there is no need to increase the amplitude of the excitation pulse to achieve a long pulse since there is minimal increase in the laser threshold. This behavior is evident in the resulting laser pulses. The pulse obtained using Rhodamine 590 is nearly triangular in shape. In this case, the excitation pulse is unable to overcome increase in laser threshold such that the laser action terminates, resulting in a laser pulse having a duration of less than one millisecond.

The pulse obtained with the dye Rhodamine 575 is more nearly constant during the first 800 microseconds. After the initial 800 microseconds, the laser threshold using Rhodamine 575 begins to rise at about the same rate as observed using the dye Rhodamine 590. By providing an excitation pulse having an increasing amplitude, as shown, wherein the excitation pulse is able to overcome the increase in laser threshold, the pulse duration is extended even further and pulses in excess of 1.5 milliseconds duration are obtainable.

Figure 4:
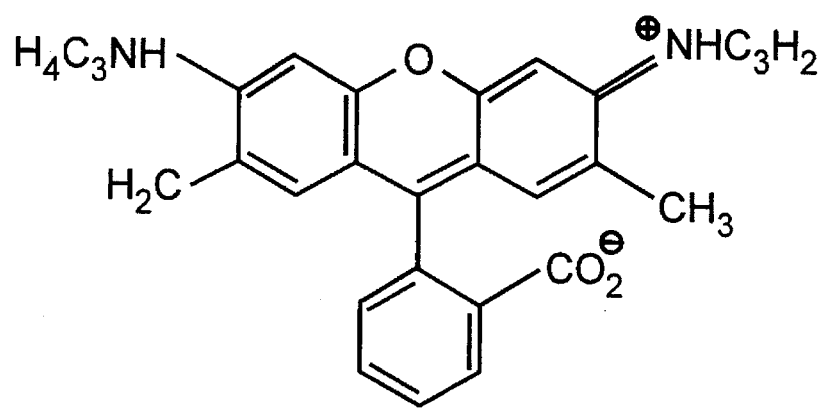
FIG. 4 is an illustration of the molecular structure of Rhodamine 575 and Rhodamine 590 dye molecules.
Figure 4:
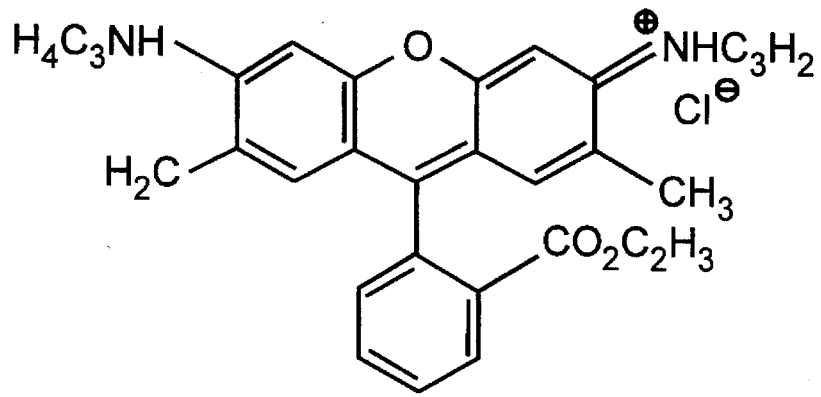

In order to generate longer laser pulses efficiently, it is advantageous to use dyes having a lasing threshold that increases slowly. FIG. 4 shows the molecular structure for Rhodamine 575 and Rhodamine 590 dyes respectively. The two structures 62 and 64 are virtually identical, except for the functional group $CO_2$ in Rhodamine 575, which is replaced with $CO_2C_2H_5$ in Rhodamine590. The $CO_2$ group is a Lewis base which comprises en electron-pair donor. More generally, the $CO_2$ group is a member of the carboxyl group, specifically a carboxylate ion. While the exact details of the photochemistry of this dye are not yet fully understood, it appears that the difference in the functionality of this group causes Rhodamine 575 to have a lasing threshold which increases at a slower rate than Rhodamine 590, resulting in longer pulses.

Equivalents

While the invention has been particularly shown and described with reference to specific preferred embodiments, it should be understood by those skilled in the art that various changes in form and detail may be made therein without departing from the spirit and scope of the invention as defined by the appended claims.

We claim:

1. A method of generating a pulsed beam of laser radiation having a long duration, comprising:

generating an excitation pulse having (i) a constant amplitude in coordination with a constant lasing threshold for a flashlamp-excited dye laser and (ii) an increasing amplitude in coordination with an increasing lasing threshold for the flashlamp-excited dye laser;

driving the flashlamp-excited dye laser with the excitation pulse; and producing a pulsed output beam of laser radiation from the flashlamp-excited dye laser of at least 500 microseconds in duration.

2. The method of claim 1 further comprising generating an excitation pulse initially having a constant amplitude, followed by an increasing amplitude.

3. The method of claim 1 wherein the pulsed output beam of laser radiation is at least one millisecond in duration.

4. The method of claim 1 wherein the flashlamp-excited dye laser comprises a dye disposed in a liquid medium.

5. The method of claim 1 wherein the flashlamp-excited dye laser comprises a dye having a molecular structure which comprises at least one electron-pair donor.

6. The method of claim 5 wherein the at least one electron-pair donor is a carboxyl group.

7. The method of claim 5 wherein the at least one electron-pair donor is a carboxylate ion.

8. The method of claim 5 wherein the dye is Rhodamine 575.

9. A method of generating a pulsed beam of laser radiation having a long duration, comprising:

provSiding a flashlamp-excited dye laser including a dye having a molecular structure which comprises at least one electron-pair donor;

generating an excitation pulse having a substantially constant amplitude in coordination with a substantially constant lasing threshold for a flashlamp-excited dye laser and an increasing amplitude in coordination with an increasing lasing threshold for the flashlamp-excited dye laser;

driving the flashlamp-excited dye laser with the excitation pulse; and producing a pulsed output beam of laser radiation of at least 500 microseconds in duration from the flashlamp-excited dye laser.

10. The method of claim 9 wherein the excitation pulse initially has a constant amplitude, followed by an increasing amplitude.

11. The method of claim 9 wherein the at least one electron-pair donor is a carboxyl group.

12. The method of claim 9 wherein the at least one electron-pair donor is a carboxylate ion.

13. The method of claim 9 wherein the dye is disposed in a liquid.

14. The method of claim 9 wherein the dye is Rhodamine 575.

* * * * *